United States Patent [19]

Engelman et al.

[11] Patent Number: 4,558,841
[45] Date of Patent: Dec. 17, 1985

[54] SPRUING ASSEMBLY

[75] Inventors: Melvin A. Engelman, Wappingers Falls; Victor Zamaloff, Poughkeepsie; Curtis L. Engelman, Wappingers Falls, all of N.Y.

[73] Assignee: Dentifax International Inc., Wappingers Falls, N.Y.

[21] Appl. No.: 579,151

[22] Filed: Feb. 10, 1984

[51] Int. Cl.[4] .......................... B22C 7/02; A61C 13/00
[52] U.S. Cl. ........................................ 249/54; 164/35; 164/244; 164/376; 164/DIG. 4; 249/62; 264/221
[58] Field of Search .................... 249/54, 55, 61, 62; 264/221, 16; 164/35, 244, DIG. 4, 34, 376, 246; 425/2

[56] References Cited

U.S. PATENT DOCUMENTS

| | | | |
|---|---|---|---|
| 1,332,878 | 3/1920 | Bard | 249/54 |
| 2,171,778 | 9/1939 | Yantis | 164/DIG. 4 |
| 2,317,008 | 4/1943 | Werner | 264/221 |
| 2,421,698 | 6/1947 | Hordes | 249/54 |
| 2,474,105 | 6/1949 | Hordes | 249/54 |
| 2,490,193 | 12/1949 | Barr | 264/221 |
| 3,064,309 | 11/1962 | Steinbock et al. | 264/221 |
| 3,249,969 | 5/1966 | Steinbock, Jr. | 164/35 |
| 3,340,923 | 9/1967 | Benfield | 164/244 |
| 3,562,365 | 2/1971 | Redgwell | 264/221 |
| 3,587,722 | 6/1971 | Slansky | 249/54 |
| 3,610,317 | 10/1971 | Benfield et al. | 164/35 |
| 3,648,760 | 3/1972 | Cooper | 164/35 |
| 3,985,178 | 10/1976 | Cooper | 164/244 |
| 4,081,019 | 3/1978 | Kulig | 164/244 |
| 4,161,208 | 7/1979 | Cooper | 164/244 |

Primary Examiner—Jay H. Woo
Assistant Examiner—James C. Housel

[57] ABSTRACT

A spruing assembly for receiving investment material in the production of an investment mold for castings by the "lost wax" process which includes a hollow chamber to receive the investment material formed by a base member and an engaging tapered ring. A horizontal feeder bar is contained within the chamber and is supported by hollow sprue means. The feeder bar is open at its top and has a narrow channel for conducting molten wax into the hollow sprue support. The base member includes a centralized sprue base former and support means associated with the former to provide support for the hollow sprue means supporting the feeder bar.

12 Claims, 5 Drawing Figures

U.S. Patent  Dec. 17, 1985  4,558,841
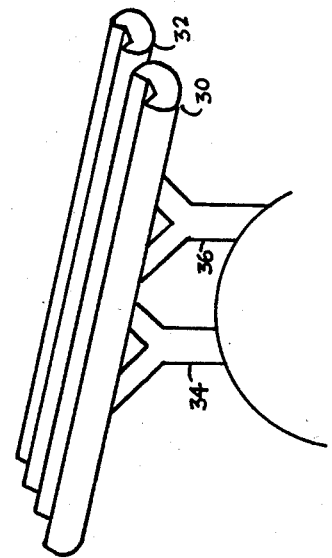
FIG. 5
FIG. 4
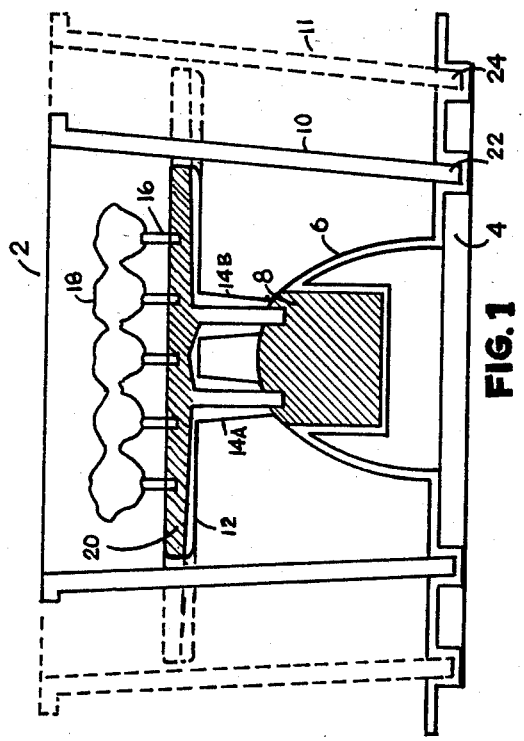
FIG. 1
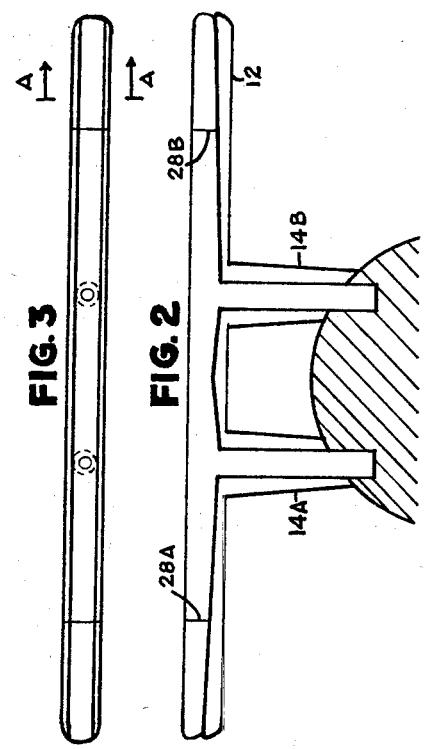
FIG. 3
FIG. 2

SPRUING ASSEMBLY

BACKGROUND OF THE INVENTION

The present invention relates to investment casting, and more specifically to a spruing assembly for receiving investment material in the production of investment mold castings.

The castings of parts such as dental items or jewelry by the lost wax process is well known. The usual method is to provide an assembly which includes a base member and a casting ring associated therewith to form a hollow chamber to receive the investment material. The casting ring may be a metal ring with an asbestos or asbestos-substitute liner that permits the investment to expand slightly to result in larger castings. Alternatively, a plastic casting ring may be used which allows unimpeded setting and thermal expansion of the investment in all directions. The base member may be formed with or include a sprue base former containing a wax plug or sprue pin apertures for supporting sprue pins. The sprue pins, or a solid horizontal plastic feeder bar supported by sprue members, provide support for a wax pattern or patterns of the parts to be cast such as crowns, bridges, pontics, copings, inlays and other such items. The hollow chamber is then filled with high heat resistant investment material which is allowed to harden or set around the wax pattern and its supporting structure. After the investment has set, the base is removed and the ring is tapped or cut away to remove the investment assembly. The investment assembly is placed in a cold burn-out oven and heated to a temperature which causes the wax pattern to melt. When all of the wax pattern, feeder bar and sprue members melt, a cavity is left into which molten metal can be poured using a casting device. After the casting operation, the investment mold is broken apart from the cooled metal; and the individual parts, such as inlays, copings, crowns or bridges, can be cut off the cast sprue assembly and fitted onto a dental model.

One of the problems that arise with this process is that, since the wax patterns melt before the solid sprue or feeder bar melts, the molten wax cannot escape from the mold. Instead, the wax is driven into the investment and the carbon in the wax can contaminate the molten alloy during casting. The resulting cast parts are not suitable for use.

Another problem associated with this process is that, as the solid plastic feeder bar is heated, it expands. As it expands, it exerts pressures within the mold sufficiently powerful to crack and damage the mold. When molten alloy is cast into this mold, it provides enough impulse to crack the mold apart. This results in a potentially dangerous shower of molten alloy. Besides the loss of the cost of the alloy, the wax patterns must also be prepared anew which is a time-consuming and painstaking process.

Still another problem that arises with this process is that as the solid feeder bar or sprue member begins to melt, it will curl and crack or chip the enveloping investment. This may cause a distorted or incomplete casting.

A further problem associated with this process is that a solid sprue or feeder bar prevents the egress of volatized wax, steam and other vapors occurring within the investment mold that is being heated. As continued heating of the mold takes place but before the plastic of the feeder bar melts, the vapor pressures that accumulate may facture the mold with the same results as detailed above.

Accordingly, it is an object of the invention to provide a spruing assembly for producing high quality castings.

Another object of the invention is to provide an improved spruing assembly which eliminates the curling of the feeder bar and possible cracking of the investment mold used in the production of metal castings.

Still another object of the invention is to provide a new and improved feeder bar for a spruing assembly designed to provide faster elimination of the molten wax and vapors through its supporting hollow sprues.

A further object of the invention is to provide a novel feeder bar for a spruing assembly which does not exert any harmful stress on surrounding investment when the bar melts during burn out.

SUMMARY OF THE INVENTION

High quality castings of individual parts by the lost wax process is achieved in accordance with the present invention by using a spruing assembly which includes a base and centralized sprue base former supporting a unique horizontal feeder bar which is open at its top and has a narrow channel for conducting molten wax into hollow sprue supporting members of the feeder bar. A plastic tapered ring is provided which engages the base member and surrounds the feeder bar to form a hollow chamber to receive investment material.

The foregoing and other objects, features and advantages of the invention will be apparent from the following particular description of a preferred embodiment of the invention, as illustrated in the accompanying drawings.

BRIEF DESCRIPTION OF THE DRAWINGS

FIG. 1 is a sectional view, partly broken away, of the spruing assembly embodying the present invention.

FIG. 2 is a sectional view of the feeder bar used in the spruing assembly of the present invention.

FIG. 3 is a top plan view of the feeder bar of FIG. 2.

FIG. 4 is a cross sectional view of the feeder bar taken on lines A—A of FIG. 3.

FIG. 5 is a view of a modified embodiment of the feeder bar which allows for multiple castings.

DETAILED DESCRIPTION

Referring to the drawings, and particularly to FIG. 1, the spruing assembly, indicated generally by reference numeral 2, constructed in accordance with the invention, includes a base member 4 having a centralized sprue base former 6 filled with a wax plug 8, a casting ring 10 supported by the base member 4 to form a hollow chamber to receive investment material and a feeder bar 12 having vertical sprue support means 14 engaging the wax plug 8 in the sprue base former 6 to thereby support and maintain the feeder bar 12 in a horizontal position. Suitable sprue pins 16 carrying a wax pattern 18 to be cast in metal are mounted in a wax strip 20 embedded into the feeder bar 12.

The base member 4 may be made of plastic material, may be annular in shape and contains a preformed sprue base former 6 at the center of the base 4. The former 6 is ellipsoidal in shape and has an opening at the top to receive the wax plug 8. Specially designed grooves 22 and 24 are provided in the base 4 to receive and securely maintain different size rings such as rings 10 or 11, respectively. This multi-groove arrangement permits different size rings to be used with the same base 4. The base 4 is reusable since it is removed after the investment material has set.

The casting rings 10 and 11 may be made of plastic material and are tapered toward the bottom of the ring to facilitate removal of the investment mold by popping it out after the final set of the investment. Removing the mold in this manner permits the ring to be reusable. The tapered shape of the rings also facilitates packaging inasmuch as the rings may be stacked within each other. The use of plastic material for the rings also permits maximum setting expansion of the investment mold because the exothermic heat of the setting investment softens the plastic and permits unimpeded expansion. The amount of expansion is increased or decreased by the amount of dilution of the liquid provided by the investment's manufacturer for mixing with the investment powder. While the plastic rings are shown in FIG. 1 as having graduated round shapes, it is within the skill of the art to use other shapes, as for example, oval shapes with, of course, the shape of the grooves of the base 4, being of similar design to receive and secure the rings in the base of the assembly. It should also be apparent that the base 4 may be designed to include a single groove for receiving and supporting a single ring especially where the size of the ring to be used is quite large or small.

Referring now to FIGS. 2 to 4, the feeder bar 12 is a plastic horizontal device that is open at its top and is supported by a pair of hollow plastic sprue members 14. The feeder bar 12 is designed to provide a narrow channel from each end of the bar and from the center of the bar downwardly toward the openings of the sprue members 14. This arrangement, when the investment mold is heated in the burn out oven, allows molten wax to be conducted into the openings of the hollow sprue members 14, leaving hollow internal spaces in the feeder bar 12 and sprue members 14. Accordingly, as the burn out process proceeds, the feeder bar 12 itself begins to melt and folds into its hollow internal space and does not exert any harmful stress which could cause cracking or chipping of the surrounding investment.

The feeder bar 12 also contains a pair of grooves 28 on the inside of bar 12 at a predetermined distance from each end of the bar 12. This distance is chosen such that the bar 12 may be used with a ring of a size such as ring 10 in FIG. 1 or with a ring of a size such as ring 11. Thus, if the feeder bar 12 is to be used with ring 10, then the ends of the bar 12, starting at the grooves, must be removed in order for the bar to fit within the ring 10 when it is placed in the proper groove 22 of the base 4. The removal may be accomplished by simply bending the feeder bar 12 at the grooves 28. On the other hand, if the feeder bar 12 is to be used with ring 11, then the feeder bar 12 may be used as is with no ends removed, and it will properly fit within ring 11. Thus, a single feeder bar is provided by the present invention which is usable with different size rings providing an economical feeder bar arrangement for a multi-ring spruing assembly.

In the casting of small parts such as dental items and the like, in accordance with the invention, a wax pattern (18) is first made over dies of prepared teeth and short sprue pins (16) are then attached to the wax pattern at their surface. A wax strip (20) is added into the length of the hollow horizontal opening of the feeder bar 12. The wax in the channel of the feeder bar is softened by application of a flame, and the feeder bar is then moved down to engage the short sprue pins in the softened wax. When the wax has cooled down and solidified, the assembly of the feeder bar and the wax patterns is removed from the dies. The vertical legs (14) of the feeder bar (12) are then inserted into the wax plug (8) of the sprue base former (6). Following this, the proper size ring (e.g., 11) is inserted into the appropriate groove (24 for ring 11) of the base (4) to form the hollow chamber for receiving the investment material. High heat resistant investment material is next poured into the ring and allowed to set for a predetermined period of time. After the investment has set, the base is removed and the tapered ring is tapped to remove the investment mold. The investment mold is then placed into a burn-out oven and heated to a high temperature. As the temperature rises, the wax in the investment mold begins to melt and is conducted along the feeder bar channel to and out the openings of the feeder bar support sprue members (14). As the temperature continues to rise, the plastic of the feeder bar begins to melt, curling into the hollow internal spaces of the feeder bar. As it continues to melt and liquify, it flows out via spaces created by the melted sprue members. After all the wax and plastic have been melted out of the mold, leaving a cavity in the mold, the investment mold is placed in a casting machine which is used to force a molten alloy such as gold, nickel-chrome or some semi-precious metal into the investment mold by the centrifugal action of the machine. After the casting is completed, the investment mold is broken away from the cooled metal and individual items can be cut off the cast assembly, cleaned, and fitted onto a dental model.

Referring now to FIG. 5, there is shown another form of feeder bar consisting of two parallel feeder bars 30 and 32 connected to two Y shaped supporting hollow sprue members 34 and 36 which seat into the wax plug of the crucible former. Each bar is open at the top and provides a narrow channel, as in the feeder bar of FIG. 2, to direct the flow of the molten wax and plastic directly to the supporting hollow sprue members and out of the mold. With this arrangement, multiple castings may be obtained with one casting operation.

While the invention has been particularly shown and described with reference to a preferred embodiment hereof, it will be understood by those skilled in the art that several changes in form and detail may be made without departing from the spirit and scope of the invention.

Having thus described my invention, what I claim as new and desire to secure by Letters Patent is:

1. A spruing assembly for receiving investment material in the production of an investment mold for castings comprising:
 a base member,
 said base member including a centralized sprue base former,
 a feeder bar,
 hollow sprue means supporting said feeder bar,
 said bar being open at its top and having a narrow channel sloping downwardly from each end of said bar toward said hollow sprue supporting means for conducting molten wax into said hollow sprue supporting means,
 a wax pattern of a part to be cast,
 wax means added to said narrow channel,
 pattern supporting means engaged by said wax means for supporting said wax pattern, said sprue base former including means for supporting said hollow sprue means, and a ring member engaging said base member and surrounding said feeder bar so as to form a hollow chamber for receiving said investment material.

2. An assembly according to claim 1 in which said base member has a groove contained therein to receive and securely maintain said ring member.

3. An assembly according to claim 1 in which said base member has multiple concentric grooves contained therein to receive and securely maintain different size ring members.

4. An assembly according to claim 1 in which said sprue supporting means consists of a wax plug inserted into an opening of said sprue base former.

5. An assembly according to claim 1 in which said feeder bar includes means for indicating where the size of said feeder bar may be altered.

6. An assembly according to claim 5 in which said indicating means is comprised of a pair of grooved indicators on the inside of said feeder bar, each being positioned a predetermined distance from the end of said feeder bar.

7. An assembly according to claim 1 in which said feeder bar consists of multiple parallel feeder elements.

8. An assembly according to claim 7 in which said sprue means is shaped to provide support for said multiple parallel feeder elements.

9. An assembly according to claim 1 in which said ring member is tapered to facilitate removal of said investment mold.

10. An assembly according to claim 1 in which said feeder bar and said hollow sprue means are formed as a unitary element.

11. An assembly according to claim 1 in which said feeder bar includes another narrow channel sloping downwardly from the center of said bar toward said hollow sprue supporting means for aiding the conduction of molten wax into said hollow sprue supporting means.

12. An assembly according to claim 1 in which said wax means comprises a wax strip added into said narrow channel, and said pattern supporting means comprises a plurality of short sprue pins engaged by said wax strip at variable points along the length of said feeder bar for supporting said wax pattern to be cast.

* * * * *